US008671481B2

(12) United States Patent
Franklin

(10) Patent No.: US 8,671,481 B2
(45) Date of Patent: Mar. 18, 2014

(54) CARDIOPULMONARY RESUSCITATION SUPPORT PILLOW

(76) Inventor: Damon Franklin, East Elmhurst, NY (US)

( * ) Notice: Subject to any disclaimer, the term of this patent is extended or adjusted under 35 U.S.C. 154(b) by 0 days.

(21) Appl. No.: 13/446,737

(22) Filed: Apr. 13, 2012

(65) Prior Publication Data

US 2012/0260428 A1 Oct. 18, 2012

Related U.S. Application Data

(60) Provisional application No. 61/475,527, filed on Apr. 14, 2011.

(51) Int. Cl.
*A61F 5/37* (2006.01)

(52) U.S. Cl.
USPC .............. 5/636; 5/637; 5/643; 5/648; 5/655.9

(58) Field of Classification Search
USPC ........................... 5/636, 637, 643, 648, 655.9
See application file for complete search history.

(56) References Cited

U.S. PATENT DOCUMENTS

| | | | | |
|---|---|---|---|---|
| 4,748,702 | A * | 6/1988 | Sandler | 5/636 |
| 4,821,355 | A * | 4/1989 | Burkhardt | 5/636 |
| 4,832,007 | A * | 5/1989 | Davis et al. | 250/580 |
| 6,446,288 | B1 * | 9/2002 | Pi | 5/636 |
| 6,471,726 | B2 * | 10/2002 | Wang | 5/636 |
| 2004/0194214 | A1 * | 10/2004 | Troop | 5/636 |
| 2005/0050636 | A1 * | 3/2005 | Setokawa | 5/636 |
| 2008/0163428 | A1 * | 7/2008 | Groteke et al. | 5/638 |
| 2009/0145442 | A1 * | 6/2009 | Hecox et al. | 128/845 |
| 2009/0222989 | A1 * | 9/2009 | Dennewald | 5/636 |
| 2009/0307846 | A1 * | 12/2009 | Eura et al. | 5/636 |
| 2011/0078860 | A1 * | 4/2011 | Sun | 5/640 |

* cited by examiner

*Primary Examiner* — William Kelleher

(57) ABSTRACT

A medical support pillow comprising of a pair of oppositely positioned sidewalls, a bottom portion having a bottom surface, and an upper portion. The support pillow includes a head support and neck support, which are dimensioned to automatically align the airways to facilitate CPR when head and neck are positioned thereupon. The upper portion has two opposing inclined surfaces. The first inclined surface for receiving and supporting the individual's neck, the second oppositely positioned inclined surface for supporting the individual's head. In a further embodiment, the medical support pillow has a circular indentation, which curves inwardly on the upper portion which hold and support and individual's neck to prevent substantial movement of the individual's head. In a further embodiment, the medical support pillow includes a hollowed out section on both right and left side of base creating handles making the medical support pillow easy to carry and transport.

5 Claims, 7 Drawing Sheets

CARDIOPULMONARY RESUSCITATION SUPPORT PILLOW

CROSS-REFERENCE TO RELATED APPLICATIONS

This application claims the benefit of provisional patent application Ser. No. 61/475,527 filed Apr. 14, 2011 by the present inventor.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable
Background—Prior Art
See attached Notice of Reference Cited

FIELD OF INVENTION

The field of the invention is a medical support pillow for facilitation of alignment of the head and neck for proper airway management during cardiopulmonary resuscitation.

BACKGROUND OF INVENTION

Cardiopulmonary resuscitation (CPR) is an emergency procedure performed in an effort to manually preserve intact brain function until further measures are taken to restore spontaneous blood circulation and breathing. It is performed on unresponsive individuals with no breathing or abnormal breathing.

Cardiopulmonary resuscitation procedure requires tilting a victim's head back to open the trachea to improve airflow to the lungs, It is very important for a CPR provider to have access to a device that maintains proper positioning of a victim during CPR and frees an emergency respondent's hands to be used in performing CPR. Ideally, such a device would accommodate a broad spectrum of people from small children to large adults.

In most emergency responses the victim's head is rested on the nearest flat surface. Currently, to accomplish the proper positioning the person attending must use his hands to properly position and hold the victim's head firmly tilting the head and lifting the chin opening the trachea to improve airflow to the lungs. Other methods commonly utilized include placing a towel under the victim's neck. However, these techniques are unreliable and may result in the failure to maintain the proper positioning of the head and neck.

What is needed is a device that will enable safe, quick, and accurate alignment of the head and neck to facilitate proper CPR. Emergency responders need a device that is lightweight and can be carried along effortlessly with other equipment.

Others have put forth designs to aid in the positioning of individuals heads and necks to facilitate breathing in emergency situations. For example, U.S. Pat. No. 6,644,288 to Pi and U.S. Pat. No. 4,918,774 to Popitz both describes a pillow for use for opening a person's airway primarily for intubation. Another example includes U.S Pat. Publ. 20090145442 to Hecox et al. that describes a medical support pillow that includes hardware and software housed within and configured to provide CPR instruction to the CPR provider. The first two-referenced support pillows were not designed specifically for providing CPR, but rather intubation and positions the patient in what is medically known as the sniffing position.

SUMMARY OF INVENTION

The medical support pillow of the present embodiment facilitates positioning the patient's head and neck in the proper position for CPR. Furthermore, by merely placing the patient's head and neck on the pillow, the patient's airways are aligned and airway open in the necessary and ready position for CPR. This embodiment provides a device enabling safe, and accurate alignment of the head tilt- chin lift position to facilitate proper CPR. The pillow is preferably sized and dimensioned to allow the victim's to be easily positioned and for individuals responding to perform CPR easily and with both hands.

The present embodiment is comprised of a base having a pair of oppositely positioned sidewalls, a bottom portion and an upper portion. The bottom portion has a bottom surface. The upper portion comprises of an inclined surface for supporting a portion of a patient's neck. This inclined surface that supports the patient's neck would be positioned at approximately a 60-degree angle. The inclined portion surface extends from a lower end to an upper end. The upper portion further includes an opposing inclined surface for supporting the patient's head. The curved surface extends from a lower end to an upper end. This opposing inclined surface supporting the patient's head would be positioned at a 45-degree angle. In a further embodiment the upper portion may also contain a circular indented cradle for support of the victim's neck to prevent substantial movement of the individual's head. However other dimensions are possible so long as they achieve the same function as the present embodiment. Similarly, the degree at which head supporting surfaces, and neck and upper back supporting surfaces may be varied, so long as proper the alignment of airway for CPR is maintained. Although pillow thereof have been described as having particular dimensions, it is to be understood that the pillow can be configured to have other dimensions suitable for any sized person, e.g. infant, child, teen, or adult.

In a further embodiment of the medical support pillow the upper portion may also contain a circular indented cradle for support of the victim's neck to prevent substantial movement of the individual's head.

In the present embodiment, the pillow would be made of durable foam. The preferred method of application would be by injection foam molding or vinyl nitride foam, making it durable, waterproof, resistant to absorption of bacteria and blood-born pathogens. This preferred embodiment would make the support pillow a lightweight device easily stored and transported by emergency responders and those performing CPR. Although pillow thereof have been described as being constructed from particular materials, it is to be understood that the present embodiment can be made from other materials such as rubber, silicone, etc.

The embodiment may also contain handles on each side making it easier for individuals to pick-up and carry. The handles can either be built in by hollowing out sections of the base or the embodiment can be fitted with attachable straps Unlike the above reference medical support pillow, this preferred embodiment would contain no electronic software making it lightweight, portable, easy to use, and manufactured at a relatively low cost.

BRIEF DESCRIPTION OF THE DRAWING

The features of the invention are believed to be novel and the elements characteristic of the invention are set forth with particularity in the appended claims. The figures are for illustration purposes only and are not drawn to scale. The invention itself, however, both as organization and method of operation, may best be understood by reference to the detailed description with the accompanying drawings, which follows:

DETAILED DESCRIPTION

The medical support pillow of the present invention for automatically aligning the airway of a patient for CPR is shown generally in FIG. 1-4*a*.

The medical support pillow comprises a base, shown generally at 1; a head support shown generally at 5 for supporting the head of the patient; and a neck support shown generally at 4, for supporting the neck of the patient, and sidewalls 2,3.

Figure 1:
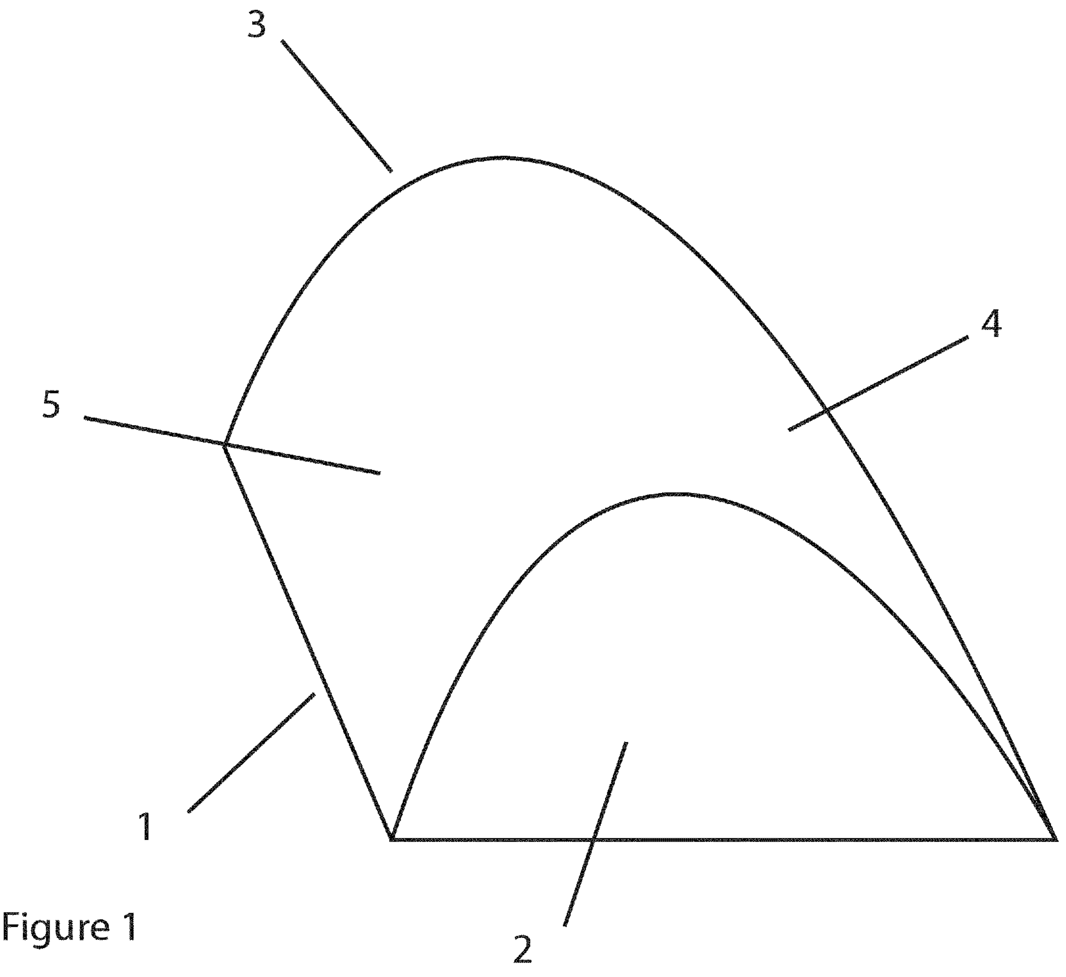
FIG. 1 is an isometric view of medical support pillow showing supportive surface for neck and right side.
Figure 1A:
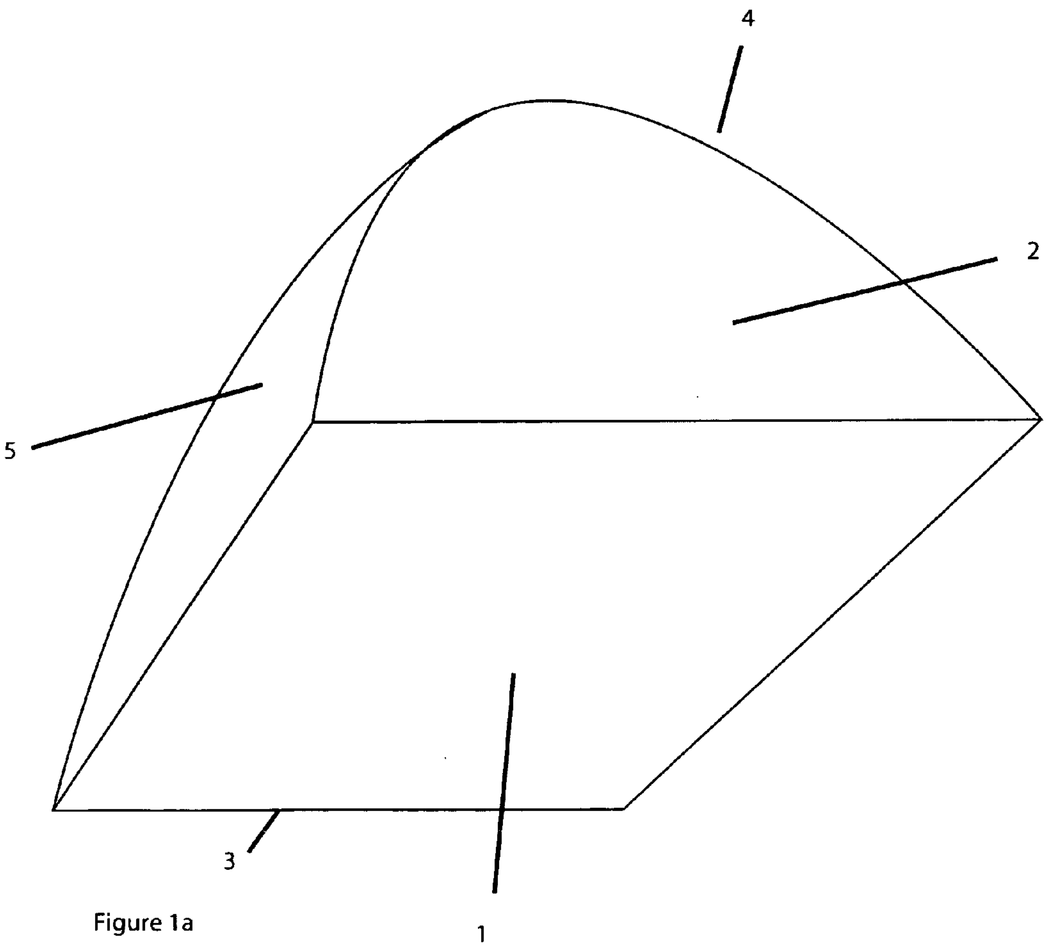
FIG. 1*a*. is an isometric view of medical support pillow showing base

Referring to FIG. 1 and 1*a*, the pillow comprises oppositely positioned sidewalls, one of which being sidewall 2, the other sidewall 3 not being shown, neck support 5 and head support 4, which is attached to the sidewalls, and bottom portion.

Figure 2:
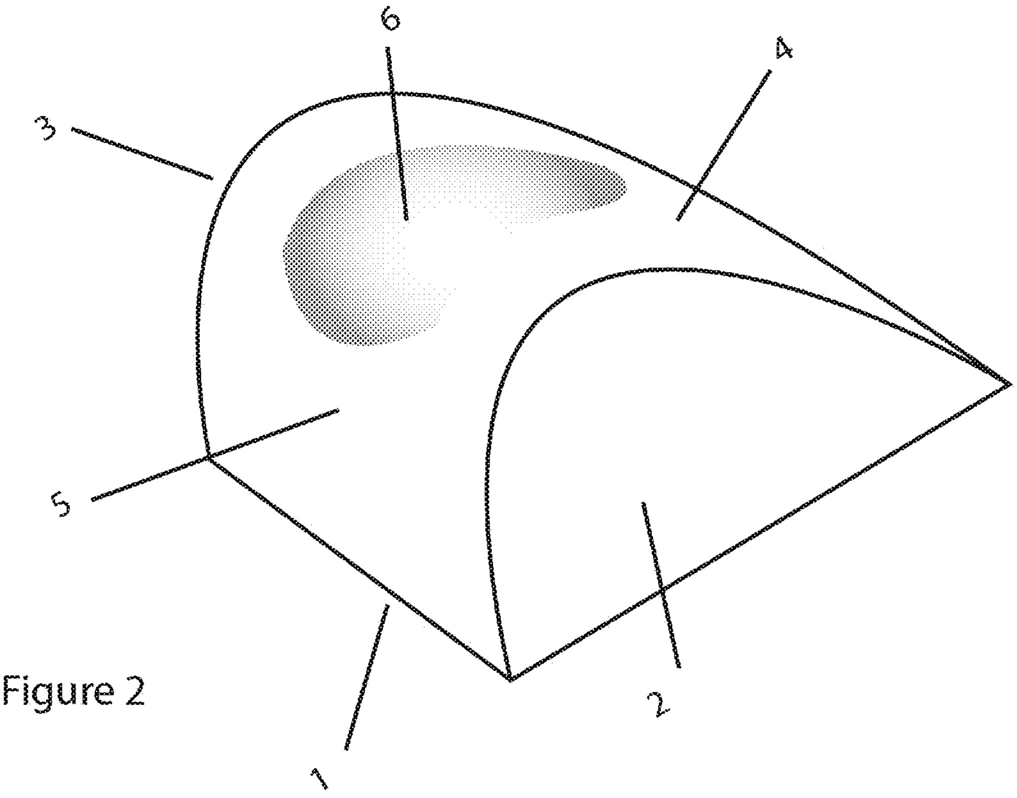
FIG. 2 is an isometric view of a of medical support pillow showing supportive surface for neck, indentation to support and hold neck and right side handle.

Referring to FIG. 2, the pillow comprises oppositely positioned sidewalls, one of which being sidewall 2, the other sidewall 3 not being shown, neck support 5 and head support 4, which is attached to the sidewalls, and bottom portion 1 not being shown, and a circular indented cradle 6 for support of the victim's neck to prevent substantial movement of the individual's head.

Figure 3:
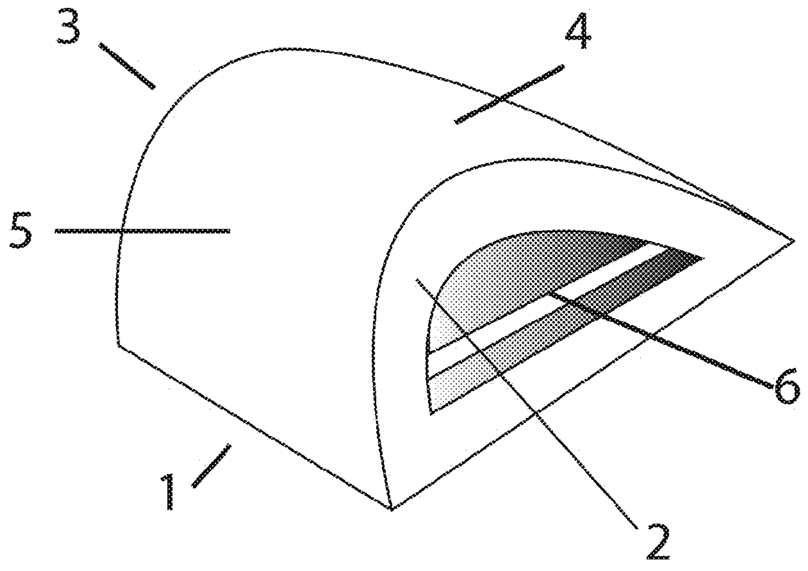
FIG. 3 is an isometric view of medical support pillow showing supportive surface for neck and right side handle.

Referring to FIG. 3, the pillow comprises oppositely positioned sidewalls, one of which being sidewall 2, the other sidewall 3 not being shown, neck support 5 and head support 4, which is attached to the sidewalls, and base 1, the bottom of each sidewall contains a section that can handles for carrying the embodiment 8, the other handle 9 not being shown created by open spaces on the right side 6, and left side not shown.

Figure 3A:
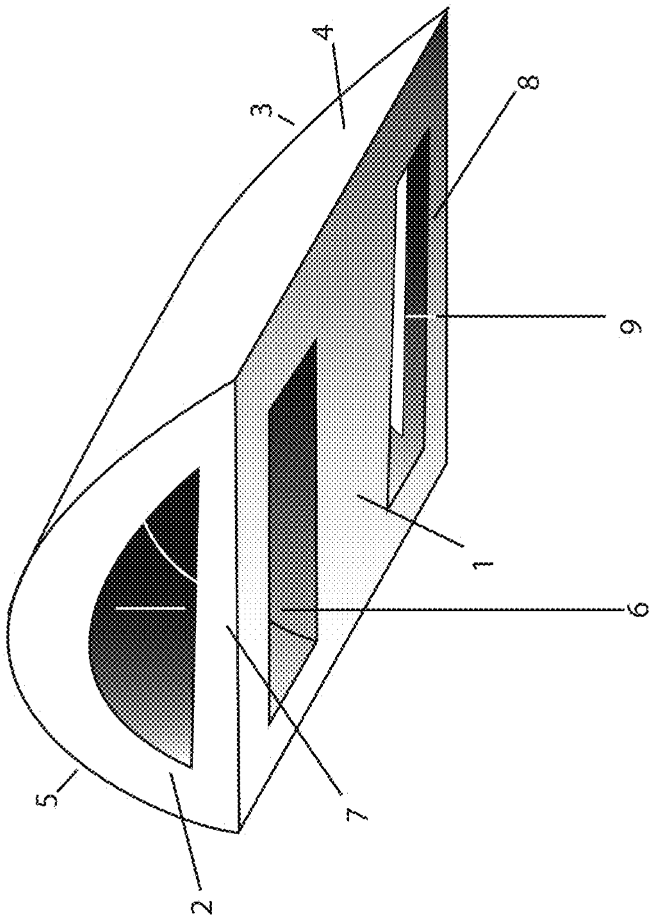
FIG. 3*a*. is an isometric view showing supportive surface for head and base with hollowed sections and left and right side handles.

Referring to FIG. 3*a*, the pillow comprises oppositely positioned sidewalls, one of which being sidewall 2, the other sidewall 3 not being shown, neck support 5 and head support 4, which is attached to the sidewalls, and base 1, the base of each sidewall contains a section that can handles for carrying the embodiment 7, 8 the created by open spaces on each side 6, 9.

Figure 4:
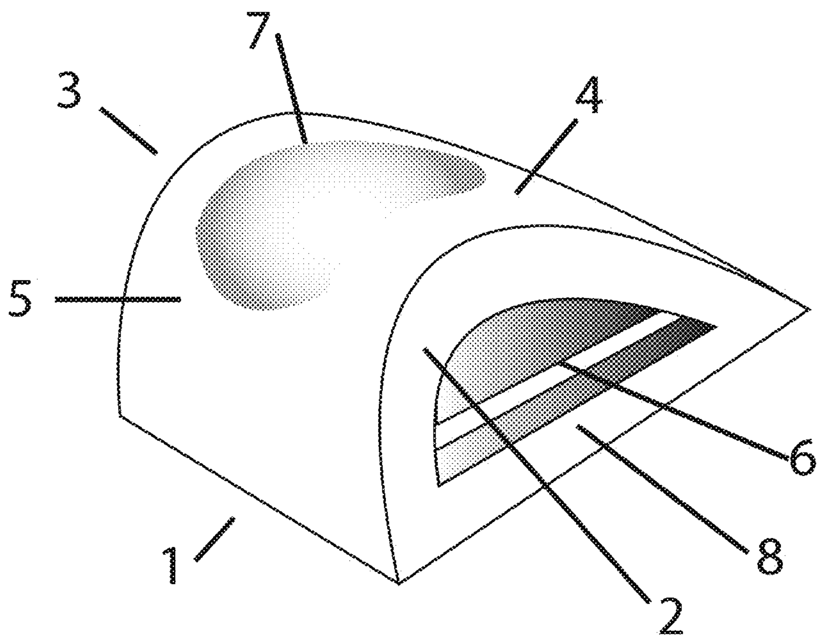
FIG. 4. is an isometric view of medical support pillow showing supportive surface for neck and head, indentation to support and hold neck and right side handle.
Figure 4A:
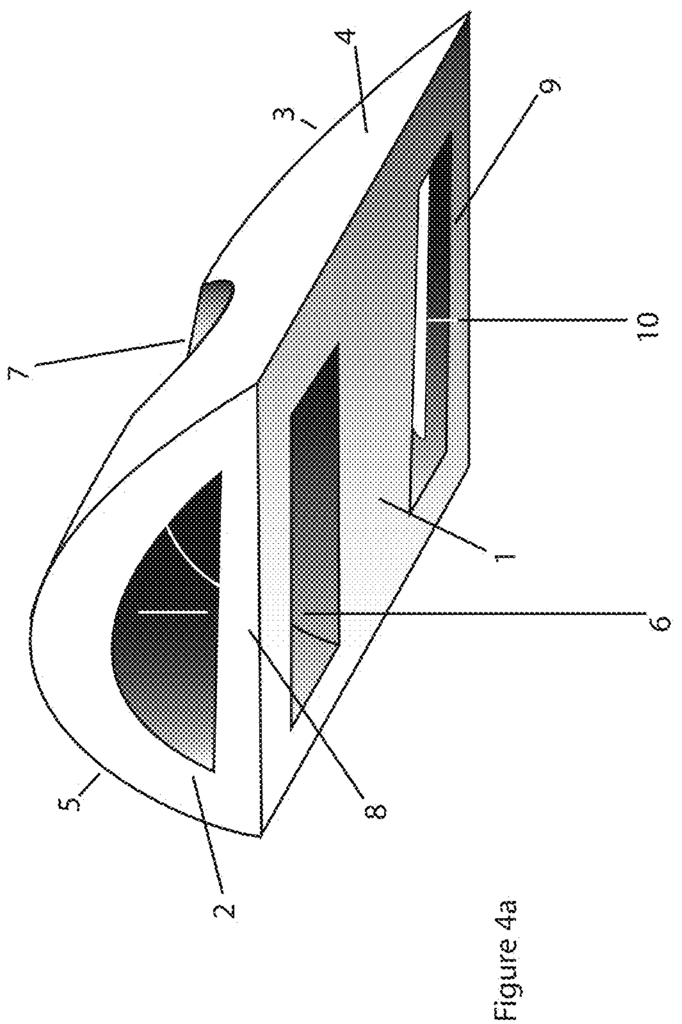
FIG. 4*a*. is an isometric view of medical support pillow showing supportive surface for head, base with hollowed sections and left and right handles.

Referring to FIG. 4. the pillow comprises oppositely positioned sidewalls, one of which being sidewall 2, the other sidewall 3 not being shown, neck support 5 and head support 4, which is attached to the sidewalls, and base 1, the base of each sidewall contains a section that can handles for carrying the embodiment 7, 8 the created by open spaces on each side 6, 9 and an indentation at the top of embodiment for securing the neck and holding it in place 7.

Referring to FIG. 1, the top back surface 4 supports the back of an individual's head while they are lying down. Additionally, the top front surface 5 supports the individual's neck, while allowing the individual's shoulders to remain in contact with the surface. The neck is placed in the indentation 7 at the top for support and keeping head in place during CPR. The top front panel for neck support 5 comprises inclined surface that extends from lower end to upper end at approximately a 60-degree angle. The top back panel 4 comprises inclined surface that extends from lower end to upper end at approximately a 45-degree angle. However, other dimensions are possible as long as they achieve the same function as the present embodiment. Similarly, the degree at which head supporting surface 4, and neck supporting surface 5, and slope may be varied, so long as proper alignment of airway for CPR is maintained.

Referring to FIG. 1 neck support 5 includes a surface that provides the necessary support for the neck of a victim. Neck support is positioned on base at neck end and extends from left side to right side. Head support 4 includes a surface that provides the necessary support for the back if a victim's head. Head support 4 extends from left side to right side.

B base 1 is preferably rectangle, although other geometric configurations are possible. The base contains two open sections on each side 6, 10 creating a handle to be used to transport the above mentioned.

Medical support pillow of the present embodiment is constructed of one or more supporting materials to form a structure for supporting the weight of a patient's neck. The preferred embodiment at present is constructed of foam applied by injection molding. One should note that one or more supporting materials could also be used without departing from scope of the inventive subject matter. For Example, pillow could be construed from rubber, plastic, or any combination of materials.

Furthermore, a disposable slipcover may be used to cover the present embodiment to prevent spread of contagious disease.

Although the foregoing description has been in terms of medical support pillow being used for purposes of CPR, it is to be understood that the pillow can be used for other purposes as well. For example pillow can be used in the performance of endotracheal intubation, and other functions used to maintain airway patency.

The principles, preferred embodiments and modes of operation of the present invention have been described in the foregoing specifications. The invention, which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

What is claimed is:

1. A support pillow for supporting and maintaining the head and neck of a patient for facilitating cardiopulmonary resuscitation (CPR) comprising:

A base member having a pair of oppositely positioned left and right sidewalls, a bottom portion having a bottom surface, and an upper portion, the upper portion comprising an inclined surface for receiving and supporting the neck and upper back of a patient, an opposing inclined surface for receiving and supporting the head of a patient, and an indentation configured to support and hold the neck of a patient, said left sidewall having a left sidewall opening, said right sidewall having a right sidewall opening, and said bottom surface having a left bottom opening and a right bottom opening, said left sidewall opening and said left bottom opening connecting together to form a left handle that is flush with said left sidewall and said bottom surface, said right sidewall opening and said right bottom opening connecting together to form a right handle that is flush with said right sidewall and said bottom surface.

2. A support pillow as set for in claim 1, wherein said upper portion comprising an inclined surface for receiving and supporting the neck and upper back of a patient extends from said left sidewall to said right sidewall.

3. A support pillow as set for in claim 1, wherein said inclined surface for receiving and supporting the head of a patient extends from said left sidewall to said right sidewall.

4. A support pillow as set forth in claim 1, wherein support pillow is constructed of non-allergenic and waterproof material which is resistant to absorption of bacteria and bloodborne pathogens.

5. A support pillow as set forth in claim 1, wherein said support pillow is made from a one-piece mold and contains no moving, removable, or electronic parts.

* * * * *